US009585867B2

(12) United States Patent
Ankner

(10) Patent No.: US 9,585,867 B2
(45) Date of Patent: Mar. 7, 2017

(54) CANNABINOD FORMULATION FOR THE SEDATION OF A HUMAN OR ANIMAL

(71) Applicant: Charles Everett Ankner, San Antonio, TX (US)

(72) Inventor: Charles Everett Ankner, San Antonio, TX (US)

(*) Notice: Subject to any disclaimer, the term of this patent is extended or adjusted under 35 U.S.C. 154(b) by 0 days.

(21) Appl. No.: 14/820,507

(22) Filed: Aug. 6, 2015

(65) Prior Publication Data
US 2015/0342922 A1 Dec. 3, 2015

(51) Int. Cl.
A61K 31/352 (2006.01)
A61K 45/06 (2006.01)

(52) U.S. Cl.
CPC ............ A61K 31/352 (2013.01); A61K 45/06 (2013.01)

(58) Field of Classification Search
CPC ..... A61K 31/66; A61K 2300/00; A61K 45/06
See application file for complete search history.

(56) References Cited

U.S. PATENT DOCUMENTS

| | | | |
|---|---|---|---|
| 3,388,136 A | 6/1968 | Taylor | |
| 3,560,528 A | 2/1971 | Petrzilka | |
| 3,668,224 A | 6/1972 | Petrzilka | |
| 3,734,930 A | 5/1973 | Razdan et al. | |
| 3,987,188 A | 10/1976 | Archer | |
| 4,025,516 A | 5/1977 | Razdan et al. | |
| 4,179,517 A | 12/1979 | Mechoulam et al. | |
| 4,279,824 A | 7/1981 | McKinney | |
| 4,376,772 A | 3/1983 | Saari et al. | |
| 4,876,276 A | 10/1989 | Mechouiam et al. | |
| 5,252,490 A | 10/1993 | ElSohly et al. | |
| 5,284,867 A | 2/1994 | Kloog et al. | |
| 5,338,753 A | 8/1994 | Burstein et al. | |
| 5,434,295 A | 7/1995 | Mechouiam et al. | |
| 5,521,215 A | 5/1996 | Mechouiam et al. | |
| 5,538,993 A | 7/1996 | Mechouiam et al. | |
| 5,605,928 A | 2/1997 | Mechouiam et al. | |
| 5,618,955 A | 4/1997 | Mechouiam et al. | |
| 5,635,530 A | 6/1997 | Mechouiam et al. | |
| 5,660,865 A | 8/1997 | Pedersen et al. | |
| 5,698,815 A | 12/1997 | Ragner | |
| 5,801,239 A | 9/1998 | Saikia et al. | |
| 5,817,657 A | 10/1998 | Beasley, Jr. et al. | |
| 5,932,610 A | 8/1999 | Shohami et al. | |
| 6,004,962 A | 12/1999 | Gooberman | |
| 6,077,537 A | 6/2000 | Booth et al. | |
| 6,113,940 A | 9/2000 | Brokke et al. | |
| 6,143,761 A | 11/2000 | Lochead et al. | |
| 6,262,112 B1 | 7/2001 | Mittendorf et al. | |
| 6,284,771 B1 | 9/2001 | Mitch et al. | |
| 6,294,192 B1 | 9/2001 | Patel et al. | |
| 6,328,992 B1 | 12/2001 | Brooke et al. | |
| 6,331,560 B1 | 12/2001 | Shohami et al. | |
| 6,365,416 B1 | 4/2002 | Elsohly et al. | |
| 6,372,768 B2 | 4/2002 | Lowe, III | |
| 6,372,799 B1 | 4/2002 | Aberg | |
| 6,403,126 B1 | 6/2002 | Webster et al. | |
| 6,410,588 B1 | 6/2002 | Feldmann et al. | |
| 6,425,764 B1 | 7/2002 | Lamson | |
| 6,469,054 B1 | 10/2002 | Mittendorf et al. | |
| 6,503,532 B1 | 1/2003 | Murty et al. | |
| 6,509,005 B1 | 1/2003 | Peart et al. | |
| 6,521,630 B1 | 2/2003 | Fliri et al. | |
| 6,531,636 B1 | 3/2003 | Mechouiam et al. | |
| 6,538,003 B1 | 3/2003 | Galli et al. | |
| 6,545,041 B2 | 4/2003 | Shohami et al. | |
| 6,545,050 B1 | 4/2003 | Mittendorf et al. | |
| 6,566,543 B2 | 5/2003 | Mechouiam et al. | |
| 6,569,463 B2 | 5/2003 | Patel et al. | |
| 6,573,278 B2 | 6/2003 | Mittendorf et al. | |
| 6,623,730 B1 | 9/2003 | Williams et al. | |

(Continued)

OTHER PUBLICATIONS

Breathes, William. Denver Westword, LLC. Published Online Jul. 17, 2014; publication verified by WaybackMachine to Mar. 8, 2015. "Dear Stoner: How much THC equals a lethal dose?". Accessed online at http://web.arch ive.org/web/20150308183212/http://www.westword.com/news/dear-stoner-how-much-thc-equals-a-lethal-dose-5124769 on May 31, 2016.*

(Continued)

Primary Examiner — Audrea Buckley
(74) Attorney, Agent, or Firm — The Roy Gross Law Firm, LLC; Roy Gross

(57) ABSTRACT

A method of humanely incapacitating or immobilizing a human or animal by providing a formulation including a cannabinoid rendering a recipient incapacitated or immobilized within a short period of time, and a delivery system which doses the recipient with the formulation resulting in a tetrahydrocannabinol blood level of above at least approximately 1-250 milligrams per milliliter of whole blood for incapacitation, or at least approximately 250-500 milligrams per milliliter of whole blood for immobilization, and below a dosage which causes irreparable harm to or the death of the recipient. Providing a delivery system to induce an incapacitating or immobilizing dose of the formulation at a distance. Providing a formulation including an antipsychotic to prevent or mitigate any violent psychosis of the recipient. Providing the formulation which induces a lethal cannabinoid blood level in the recipient which causes the death of the recipient within a humane period of time after formulation administration.

14 Claims, No Drawings

(56) References Cited

U.S. PATENT DOCUMENTS

| | | |
|---|---|---|
| 6,635,237 B2 | 10/2003 | Lowenstein et al. |
| 6,645,747 B1 | 11/2003 | Hallahan et al. |
| 6,713,048 B2 | 3/2004 | Peart et al. |
| 6,720,001 B2 | 4/2004 | Chen et al. |
| 6,727,279 B2 | 4/2004 | Mittendorf et al. |
| 6,730,330 B2 | 5/2004 | Whittle et al. |
| 6,730,519 B2 | 5/2004 | Elsohly et al. |
| 6,734,176 B2 | 5/2004 | Achard et al. |
| 6,787,530 B1 | 9/2004 | Goodchild et al. |
| 6,858,603 B2 | 2/2005 | Achard et al. |
| 6,864,291 B1 | 3/2005 | Fride et al. |
| 6,878,716 B1 | 4/2005 | Castelhano et al. |
| 6,903,137 B2 | 6/2005 | Fride et al. |
| 6,923,988 B2 | 8/2005 | Patel et al. |
| 6,946,150 B2 | 9/2005 | Whittle |
| 6,949,582 B1 | 9/2005 | Wallace |
| 6,979,689 B2 | 12/2005 | Gonzales et al. |
| 6,997,110 B2 | 2/2006 | Rastegar |
| 7,025,992 B2 | 4/2006 | Whittle et al. |
| 7,034,013 B2 | 4/2006 | Thompson et al. |
| 7,041,705 B2 | 5/2006 | Mishra et al. |
| 7,081,471 B2 | 7/2006 | Lippa et al. |
| 7,094,930 B2 | 8/2006 | Quallich et al. |
| 7,214,716 B2 | 5/2007 | Fride et al. |
| 7,231,875 B2 | 6/2007 | Rastegar |
| 7,234,399 B2 | 6/2007 | Rastegar |
| 7,273,737 B2 | 9/2007 | Hallahan et al. |
| 7,297,796 B2 | 11/2007 | Dolle et al. |
| 7,325,548 B2 | 2/2008 | Enslin |
| 7,326,735 B2 | 2/2008 | Bell et al. |
| 7,344,736 B2 | 3/2008 | Whittle et al. |
| 7,345,038 B2 | 3/2008 | Bright et al. |
| 7,378,418 B2 | 5/2008 | Yu et al. |
| 7,399,872 B2 | 7/2008 | Webster et al. |
| 7,402,686 B2 | 7/2008 | Duchek |
| 7,473,689 B2 | 1/2009 | Feldman et al. |
| 7,528,127 B2 | 5/2009 | Feldman et al. |
| 7,544,676 B2 | 6/2009 | Dolle et al. |
| 7,581,540 B2 | 9/2009 | Hale et al. |
| 7,597,910 B2 | 10/2009 | McDowell, Jr. |
| 7,622,140 B2 | 11/2009 | Whittle et al. |
| 7,648,696 B2 | 1/2010 | McPhillips et al. |
| 7,671,052 B2 | 3/2010 | Dolle et al. |
| 7,700,368 B2 | 4/2010 | Flockhart et al. |
| 7,709,536 B2 | 5/2010 | Whittle |
| 7,749,953 B2 | 7/2010 | Bab et al. |
| 7,754,680 B2 | 7/2010 | Cunningham et al. |
| 7,759,526 B2 | 7/2010 | Mechouiam et al. |
| 7,884,133 B2 | 2/2011 | Mechouiam et al. |
| 7,968,594 B2 | 6/2011 | Guy et al. |
| 8,034,843 B2 | 10/2011 | Whittle et al. |
| 8,071,641 B2 | 12/2011 | Weiss et al. |
| 8,110,569 B2 | 2/2012 | Putman et al. |
| 8,119,697 B2 | 2/2012 | Mechoulam et al. |
| 8,124,839 B2 | 2/2012 | Park et al. |
| 8,198,327 B2 | 6/2012 | Mechoulam et al. |
| 8,211,946 B2 | 7/2012 | Whittle |
| 8,227,627 B2 | 7/2012 | Stinchcomb et al. |
| 8,247,609 B2 | 8/2012 | Roques et al. |
| 8,252,973 B2 | 8/2012 | Pojer et al. |
| 8,278,308 B2 | 10/2012 | Leone-Bay et al. |
| 8,293,211 B2 | 10/2012 | Makriyannis et al. |
| 8,314,083 B2 | 11/2012 | Du |
| 8,337,908 B2 | 12/2012 | Letzel et al. |
| 8,378,277 B2 | 2/2013 | Sandomirsky et al. |
| 8,389,480 B2 | 3/2013 | Kuliopulos et al. |
| 8,425,950 B1 | 4/2013 | Santillan et al. |
| 8,425,954 B2 | 4/2013 | Stone |
| 8,445,034 B1 | 5/2013 | Coles, Jr. |
| 8,454,945 B2 | 6/2013 | McCook et al. |
| 8,470,874 B2 | 6/2013 | Musty et al. |
| 8,481,091 B2 | 7/2013 | Ross |
| 8,497,299 B2 | 7/2013 | Mechoulam et al. |
| 8,512,767 B2 | 8/2013 | Ross |
| 8,518,653 B2 | 8/2013 | Takkinen et al. |
| 8,555,875 B2 | 10/2013 | Cook et al. |
| 8,578,919 B2 | 11/2013 | Macy et al. |
| 8,603,515 B2 | 12/2013 | Whittle |
| 8,629,177 B2 | 1/2014 | Castor et al. |
| 8,642,645 B2 | 2/2014 | Kelly |
| 8,673,368 B2 | 3/2014 | Guy et al. |
| 8,722,938 B2 | 5/2014 | Mechoulam et al. |
| 8,728,544 B1 | 5/2014 | Pritchett |
| 8,771,760 B2 | 7/2014 | Guy et al. |
| 8,778,418 B2 | 7/2014 | Bisterfeld Von Meer |
| 8,808,734 B2 | 8/2014 | Winnicki |
| 8,846,409 B2 | 9/2014 | Flockhart et al. |
| 8,884,100 B2 | 11/2014 | Page et al. |
| 8,895,061 B2 | 11/2014 | Balwani et al. |
| 8,906,429 B1 | 12/2014 | Kolsky |
| 8,910,630 B2 | 12/2014 | Todd |
| 8,975,245 B2 | 3/2015 | Goodchild et al. |
| 8,980,941 B2 | 3/2015 | Hospodor |
| 8,980,942 B2 | 3/2015 | Stinchcomb et al. |
| 9,017,737 B2 | 4/2015 | Kikuchi et al. |
| 9,023,322 B2 | 5/2015 | Van Damme et al. |
| 9,034,395 B2 | 5/2015 | Whittle et al. |
| 9,035,130 B2 | 5/2015 | De Meijer |
| 9,044,390 B1 | 6/2015 | Speier |
| 9,066,910 B2 | 6/2015 | Rosenblatt et al. |
| 9,066,920 B2 | 6/2015 | Whalley et al. |
| 2002/0031480 A1* | 3/2002 | Peart .................. A61K 9/008 424/45 |
| 2003/0041768 A1 | 3/2003 | Rastegar |
| 2003/0106545 A1 | 6/2003 | Verini |
| 2005/0203068 A1* | 9/2005 | Wingard ............. A61K 31/66 514/130 |
| 2007/0101891 A1 | 5/2007 | Rastegar |
| 2007/0101892 A1 | 5/2007 | Rastegar |
| 2007/0151551 A1 | 7/2007 | Verini |
| 2008/0112895 A1 | 5/2008 | Kottayil et al. |
| 2010/0292345 A1 | 11/2010 | Pertwee |
| 2012/0211591 A1 | 8/2012 | Sandomirsky et al. |
| 2013/0047481 A1 | 2/2013 | Macy et al. |
| 2013/0059018 A1 | 3/2013 | Parolaro et al. |
| 2013/0089600 A1 | 4/2013 | Winnicki |
| 2014/0302148 A1 | 10/2014 | Winnicki |

OTHER PUBLICATIONS

Shafer, Raymond P., Marihuana, A Signal of Misunderstanding, National Commission on Marihuana and Drug Abuse, 1972, Washington D.C. GPO, USA.

Martin A. Lee, Synthetic Pot As a Milatry Weapon? Meet the Man Who Ran the Secret Program, AlterNet, Internet News Service, (http://www.alternetorg/), Jul. 18, 2008, (http://www.alternet.org/story/92049/synthetic_pot_as_a_military_weapon_meet_the_man_who_ran_the_secret_program), Independent Media Institute (IMI) 77 Federal Street—Second Floor San Francisco, CA 94107.

Raffi Khatchadourian, Operation Delirium Decades after a risky Cold War experiment, a scientist lives with secrets., The New Yorker Magazine (http://www.newyorker.com/), Dec. 17, 2012, (http://www.newyorker.com/magazine/2012/12/17/operation-delirium), The New Yorker, 1 World Trade Center, New York, NY 10007.

James S. Ketcum, M.D., Chemical Warfare Secrets Almost Forgotten, A Personal Story of Medical Testing of Army Volunteers with Incapacitating Chemical Agents During the Cold War (1955-1975), 2006-2007, pp. 35-42, ISBN 9781424300808, ChemBooks Inc., Santa Rosa, California 95403 USA.

Joan T. Pickens, Sedative Activity of Cannabis in Relation to Its delta-trans-Tetrahydrocannabinol, British Journal of Pharmacology, (1981), 72, 649-656, 1981, Macmillan Publishers Ltd, The Macmillan Building, 4 Crinan St, London N1 9XW, United Kingdom.

Frederick H. Meyers, M.D., Pharmacology of Marijuana: Just Another Sedative, The Drug Policy Foundation's CME Seminar,

(56) References Cited

OTHER PUBLICATIONS

Nov. 13, 1992, Washington D.C. (available on Oct. 5, 2106 at: http://druglibrary.org/Schaffer/library/marij.htm.).

* cited by examiner

CANNABINOD FORMULATION FOR THE SEDATION OF A HUMAN OR ANIMAL

FIELD OF THE INVENTION

The present inventive method relates to a pharmaceutical sedation formulation for quickly and safely rendering a subject intoxicated, incapacitated, and/or immobilized within a short period after administration. The formulation also allows for a safer approach and subduing of a subject within a short period of time after dosing, and continues to render the subject safe for handling and/or transport for hours, without harm to or death of the subject. The formulation may include at least one cannabinoid from or derived from plants of the Cannabaceae sensu stricto family, and more specifically plants of the *C. Cannabis* L. genera.

BACKGROUND OF THE INVENTION

"In the beginning God made heaven and earth . . . . Then God said, 'Behold, I have given you every seed-bearing herb that sows seed on the face of all the earth, and every tree whose fruit yields seed; to you it shall be for food. I also give every green plant as food for all the wild animals of the earth, for all the birds of heaven, and for everything that creeps on the earth in which is the breath of life.' It was so. Then God saw everything He had made, and indeed, it was very good. So evening and morning were the sixth day." Book of Genesis, Chap 1:1, 29-31, commonly attributed to "the Yahwist", circa 5th Century B.C.E, as translated and interpreted in *The Orthodox Study Bible: Ancient Christianity Speaks to Today's World*, Thomas Nelson Publishing, 2008, USA.

" . . . the greatest service which can be rendered to any country is to add a useful plant to its culture; especially a bread grain, next in value to bread, is oil.", Thomas Jefferson, 3rd President of the United States of America, *Memorandum of Services to My Country*, 1800, Charlottesville, Va. USA.

"Damn it Charles, no damn good will ever come of this *cannabis* crap! Plus, it's illegal!" Excited utterance of Frank G. Ankner, father and grandfather of instant co-inventors, 1978, Lake Worth, Fla. USA.

Since antiquity, the Cannabaceae sensu stricto ("s.s.") family of plants have had a wide variety of innovative uses, with some varieties being used for and as food, spice, and ceremonial purposes as early as 8000 B.C.E. Modern uses of the Cannabaceae s.s. family include; varieties being cultivated for plant fiber used in almost innumerable products, varieties being cultivated containing flavonoid and aromatic substances used in the production of beer and in fragrances, varieties being cultivated for human and animal consumption, varieties being cultivated for oil as illumination and lubrication, and being cultivated for oil as bio-fuel replacements for fossil-fuel, and varieties cultivated which contain powerful antimicrobial substances used as sanitizers, antibiotics, and being researched as anti-cancer agents.

Many cultural anthropologists and ethnobotanists hold that *C. cannabis* L. varieties are among the first plants cultivated by humanity. Modernly, *C. cannabis* L. varieties are cultivated and utilized extensively and world-wide. Stems, branches, and leaves are used for plant fiber and as biofuel; sprouts and seeds as food-stocks; seeds for inexpensive lubrication and illumination oil, and also as biofuel; flowers for aromatic, recreational, ritual, sacramental, and medicinal purposes; and flowers and roots for medicinal and pharmaceutical formulations.

Recently, substances in some *C. cannabis* L. varieties have been used to effectively eradicate both MRSA and ORSA bacterium (Methicillin-Resistant *Staphylococcus aureus* and Oxacillin-Resistant *Staphylococcus aureus*), occurring both in and ex vivo. MRSA and ORSA are both extremely virulent, antibiotic resistant, strains of bacterium which sicken millions and cause hundreds of thousands of deaths per-year world-wide; particularly in industrialized nations. Research continues into using *C. cannabis* L. variety substances as and in sanitizers and antibiotics which kill pathogens like MRSA and ORSA, and other drug resistant pathogens.

It is well known in the fields of non-lethal and less-than-lethal weapons that humanely rendering a subject (either human or animal) "compliant to commands", "safe to approach and subdue", and/or to render a subject unconscious or unresponsive immediately or within a short period of time—would save lives in many critical and life-threatening situations. Further, if a subject remained incapacitated or immobilized for a long period of time, minutes to hours, taking the subject into lawful custody or containment would be safer for both the subduer as well as the subdued. Providing an effective, instantaneous or near-instantaneous, non-lethal or less-than-lethal, option or method for subduing an already intoxicated, psychotic, extremely agitated, violent or nonviolent recipient or offender would indeed be a true God-send. Goals of both military and civilian law enforcement personal are to keep the peace and save lives. Both goals may be better accomplished via the instant inventive cannabinoid sedative formulation and associated delivery system.

Known non-lethal or less-than-lethal weapons and techniques include but are not limited to: so-called "Taser" guns, rubber, wax, or plastic bullets, "bean-bag" bullets, airfoil projectiles, tear-gas, mace, pepper-spray, and the like, or other psychochemical warfare agents or methods. Although never developed into effective weapons systems in the context of the Cold War, psychochemical warfare theory and research, along with overlapping mind control drug research, was secretly pursued in the mid-20th century by the U.S. Military and Central Intelligence Agency. These research programs were ended when they came to light and generated controversy in the 1970s. The degree to which the Soviet Union developed or deployed similar chemical agents during the same period remains largely unknown. This course of human events during that time hindered or prohibited *cannabis, cannabis*-derived, or synthetic-cannabinoids from being developed into safe and effective non-lethal sedatives and non-lethal psychochemical weapons. In the 1970s, with the U.S. categorizing *cannabis* as a Schedule 1 Controlled Substance, touting *cannabis* as an effective and safe sedation or psychochemical warfare agent would have been prohibited by then public policy and law. Possibly now fifty years later, executive governmental agencies, legislatures, law enforcement, civilian defenders, and medical science may now be amenable to just such an effective method to counter the ever changing and ever present threats to life and limb in today's dangerous world, and to do so in a humane, effective, and non-lethal manner.

In the fields of veterinary science, zoology, zoo-keeping, animal husbandry, animal control, and in many related fields of endeavor, so-called "tranquilizing" apparatus, formulations, and methods are well known and widely used.

Advantageously, a humane cannabinoid formulation may be used as and for quickly and safely sedating a subject within a short period of time, thus making subduing, and if required, containing the subject safer for all involved.

Additionally, and depending upon the cannabinoid formulation, a human or animal may be quickly incapacitated or immobilized at a distance. The purpose of and for incapacitating or immobilizing a human or animal may be many and varied. It is contemplated that the fields of medicine, veterinary medicine and science, military combat, law enforcement, corrections, emergency response, mass casualty response, and similar fields of endeavor may benefit from cannabinoid sedative formulations, or a cannabinoid being added to or administered with known sedative formulations for medical, scientific, and industrial purposes. Other cannabinoid sedative formulations may be also used for scientific and industrial use improvement and purposes.

Cannabinoids were first discovered in the 1940s when cannabidol (herein "CBD") and cannabinol ("CBN") were scientifically identified and designated. The structure of tetrahydrocannabinol ("THC") was not scientifically identified and designated until 1964.

Due to molecular similarity and ease of synthetic conversion, CBD was originally believed to be a natural precursor to and of THC. However, it is now known that CBD and THC are produced independently in the *cannabis* plant from the precursor cannabigerol ("CBG").

At present, at least 85 different cannabinoids have been isolated and identified from *cannabis* plants. Cannabinoids are a class of diverse chemical compounds that among other actions, act on cannabinoid receptors in cells that repress neurotransmitter release in the brains of humans and animals. Ligands have at least one donor atom with an electron pair used to form covalent bonds with the central atom. Ligands for these receptor proteins include endo-cannabinoids (produced naturally in the body), phyto-cannabinoids (found in *cannabis* and some other plants), and synthetic-cannabinoids (those manufactured artificially).

The most notable cannabinoid is the phyto-cannabinoid tetrahydrocannabinol (herein "THC") which is thought to be the primary psychoactive component of *cannabis*. Cannabidiol (herein "CBD") and cannabinol (herein "CBN") are other major cannabinoids of *C. Cannabis* L plants. It is believed there are yet unknown phyto-cannabinoids to be scientifically isolated from *cannabis* which may exhibit varied effects and affects on and in humans and animals.

*Cannabis*, and other phyto-cannabinoid producing plants, exhibit wide variation in the quantity, quality, and type of cannabinoids they produce. The mixture of phyto-cannabinoids produced by a plant is typically known as the plant's phyto-cannabinoid "profile" or "presentation". Selective breeding has been used to influence plant genetics and modify the phyto-cannabinoid presentation. For example, strains that are used as fiber (commonly called industrial hemp) are bred such that they are low in psychoactive chemicals like THC. Strains used in medicine are often bred for high CBD content, and strains used for recreational purposes are usually bred for high THC content, or for a specific desired phyto-cannabinoid balance or profile.

Quantitative analysis of a plant's phyto-cannabinoid profile is often determined by gas chromatography, or more reliably gas chromatography combined with mass spectrometry. Liquid chromatography techniques are also possible, and unlike gas chromatography methods can differentiate between the acid and neutral forms of a phyto-cannabinoid. There have been attempts to systematically monitor the phyto-cannabinoid profile of *cannabis* over time, but their accuracy has been impeded by prohibitive controlled substance classification status of the *cannabis* plant in many countries.

Before the 1980s, it was speculated that phyto-cannabinoids produced their physiological and psychoactive effects via nonspecific interaction with cell membranes, instead of in reality interacting with specific cell membrane bound receptors. Discovery of the first cannabinoid receptors in the 1980s resolved the debate. Cannabinoid receptors are common in animals, and have been found in mammals, birds, fish, and reptiles. At present, there are two known types of cannabinoid receptors designated CB1 and CB2—with scientific evidence mounting of more cannabinoid receptors yet to be identified.

CB1 receptors are found primarily in the brain, and more specifically in the basal ganglia and limbic system including the hippocampus. CB1 receptors are also found in the cerebellum. The human brain has more cannabinoid receptors, both CB1 and CB2, than any other G protein-coupled receptor ("GPCR") type. Both human male and female reproductive systems also include CB1 receptors.

Advantageously however, CB1 receptors are absent in the medulla oblongata, the part of the brain stem responsible for autonomic respiratory and cardiovascular function. This is highly advantageous when cannabinoids are used for and as sedative and anesthetic formulations. Affecting or depressing autonomic respiratory and/or cardiovascular function has long been a limiting disadvantage of known sedative and anesthetic formulations. Fortunately, unless introduced at extremely toxic levels, CB1 agonist cannabinoids primarily leave autonomic respiratory and cardiovascular functions in humans and animals unaffected, due to the lack of CB1 receptors in the brain stem medulla oblongata.

CB2 receptors are predominantly found in the immune system, and in immune-derived cells of humans and animals—with the greatest density being in the spleen. While found only in the peripheral nervous system, some studies indicate that CB2 is expressed by a subpopulation of microglia in the human cerebellum. CB2 receptors appear to be responsible for the known anti-inflammatory and possibly other therapeutic affects and effects of *cannabis*.

*Cannabis*-derived phyto-cannabinoids are primarily concentrated in viscous resin produced in structures known as "glandular trichomes" of the *cannabis* plant. All phyto-cannabinoid classes are thought to be derived from CBG type compounds and differ mainly in the way this precursor is cyclized. Classical phyto-cannabinoids are derived from their respective 2-carboxylic acids (2-COOH) by decarboxylation (catalyzed by heat, light, or alkaline conditions). These include but are not limited to CBG (Cannabigerol), CBC (Cannabichromene), CBL (Cannabicyclol), CBV (Cannabivarin), THCV (Tetrahydrocannabivarin), CBDV (Cannabidivarin), CBCV (Cannabichromevarin), CBGV (Cannabigerovarin), and CBGM (Cannabigerol monomethyl ether).

THC is the primary psychoactive component of the *cannabis* plant. Delta-9-tetrahydrocannabinol and delta-8-tetrahydrocannabinol mimic the action of anandamide ("AEA"), a neurotransmitter produced naturally in the body of humans and animals. These two phyto-cannabinoids produce the classic psychoactive affects and effects associated with *cannabis* by binding to CB1 receptors in the brain. THC appears to act as an analgesic to ease moderate-to-severe pain, and act as a neuroprotective while also offering the potential to reduce neuroinflammation and to stimulate neurogenesis. THC seems to have approximately equal affinity for CB1 and CB2 receptors.

CBD is not psychoactive and at first was thought to not affect the psychoactivity of THC. However, recent evidence shows that *cannabis* users prone to psychosis while using high THC to CBD ratio *cannabis* had fewer and less extreme psychotic-like symptoms using high CBD to THC ratio *cannabis*. Some research suggests that the antipsychotic affects of CBD potentially represent a novel mechanism in the treatment of schizophrenia and other affective disorders. CBD has little affinity for CB1 and CB2 receptors, but acts as an indirect antagonist of cannabinoid agonists. Recently, CBD was found to be an antagonist at the putative new cannabinoid receptor GPR55, a GPCR expressed in the caudate nucleus and putamen of the brain. CBD appears to relieve convulsion, inflammation, anxiety, and nausea, and has a greater affinity for the CB2 receptor than for the CB1, although the overall affinity to both is weak. CBD shares a precursor with THC and is the main cannabinoid in low-THC *cannabis* strains. CBD also apparently plays a role in preventing the short-term memory loss associated with THC in mammals. CBD has also been shown to act as a 5-HT1A receptor agonist. Some beneficial effects observed from 5-HT1A receptor activation are decreased aggression, increased sociability, decreased impulsivity, inhibition of drug-seeking behavior, facilitation of sex drive and arousal, inhibition of penile erection, decreased food intake, prolonged REM sleep latency, and reversal of opioid-induced respiratory depression.

Researchers at California Pacific Medical Center have discovered CBD's ability to "turn off" the activity of ID1, a gene responsible for metastasis in breast and other types of cancers, including aggressive triple negative breast cancer.

CBN is primarily a product of THC degradation, and there is usually little CBN in living or freshly harvested *cannabis*. CBN content increases as THC degrades in storage and with exposure to light and air. CBN is only mildly psychoactive, and its affinity to the CB2 receptor is higher than to the CB1.

Many ethnobotanists, organic chemists, biochemists, and medical professionals consider THC, CBD, and CBN to be the "big three" of phyto-cannabinoids and *cannabis*, and of which's ratio primarily effects the profile or presentation of a specific *cannabis* variety.

Cannabigerol ("CBG") is non-psychotomimetic but still impacts the overall effects and affects of *cannabis*. CBG acts as a α2-adrenergic receptor agonist, 5-HT1A receptor antagonist, CB1 receptor antagonist, and also binds to the CB2 receptor.

Tetrahydrocannabivarin ("THCV") is prevalent in certain central Asian and southern African strains of *cannabis*. It is an antagonist of THC at CB1 receptors and attenuates the psychoactive effects of THC. The psychoactive effects of THCV in *cannabis* and *cannabis* formulations are not yet well characterized. Unlike THC, CBD, and cannabichromene ("CBC"), THCV doesn't begin as cannabigerolic acid ("CBGA"). Instead of combining with olivetolic acid to create CBGA, geranyl pyrophosphate joins with divarinolic acid, which has two less carbon atoms. The result is cannabigerovarin acid ("CBGVA"). Once CBGVA is created, the process continues as it would for THC. CBGVA is broken down to tetrahydrocannabivarin carboxylic acid ("THCVA").

Cannabidivarin ("CBDV") usually comprises a minor part the *cannabis* phyto-cannabinoid profile. Enhanced levels of CBDV have been reported in feral *cannabis* plants of the northwest Himalayas and in hashish from Nepal. GW Pharmaceuticals is actively developing a CBDV based formulation due to CBDV's demonstrated neurochemical pathway for previously observed antiepileptic and anticonvulsive affects.

Cannabichromene ("CBC") is non-psychoactive, does not affect the psychoactivity of THC, and is more common in tropical *cannabis* varieties. CBC exhibits anti-inflammatory and analgesic properties. Evidence suggests that CBC may play a role in anti-inflammatory and anti-viral effects, and may contribute to the overall analgesic effects of *cannabis*. One study in 2010 showed that CBC along with CBD and THC has antidepressant affects. Another study showed that CBC helps promote neurogenesis.

Cannabinoid production in *cannabis* starts when an enzyme causes geranyl pyrophosphate and olivetolic acid combine and form CBGA. Next, CBGA is independently converted to either CBG, THCA, CBDA or CBCA by four separate synthase, FAD-dependent dehydrogenase enzymes. There is no evidence for enzymatic conversion of CBDA or CBD to THCA or THC. For the propyl homologues (THCVA, CBDVA and CBCVA), there is an analogous pathway that is based on CBGVA from divarinolic acid instead of olivetolic acid.

Each of the cannabinoids above may be in different forms depending on the position of the double bond in the alicyclic carbon ring. There is potential for confusion because there are different numbering systems used to describe the position of this double bond. Under the dibenzopyran numbering system widely used today, the major form of THC is called Δ9-THC, while the minor form is called Δ8-THC. Under an alternate terpene numbering system, these same compounds are labeled Δ1-THC and Δ6-THC, respectively. Accordingly, herewithin tetrahydrocannabinol and/or "THC" shall be defined to include the delta-9-tetrahydrocannabinol, delta-8-tetrahydrocannabinol, delta-1-tetrahydrocannabinol, and delta-6-tetrahydrocannabinol designations.

Most classical cannabinoids are twenty-one-carbon compounds. However, some do not follow this rule primarily because of variation in the length of the side-chain attached to the aromatic ring. In THC, CBD, and CBN, this side-chain is a pentyl (five-carbon) chain. In the most common homologue, the pentyl chain is replaced with a propyl (three-carbon) chain. Cannabinoids with the propyl side-chain are named using the suffix varin, and are designated, for example, THCV, CBDV, or CBNV.

Phyto-cannabinoids are known to occur in several plant species besides *cannabis*. These include but are not limited to *echinacea purpurea, echinacea angustifolia, echinacea pallida, acmella oleracea, helichrysum umbraculigerum*, and *radula marginata*. The best-known cannabinoids that are not derived from *cannabis* are the lipophilic alkamides (alkylamides) from the *echinacea* species, most notably the cis/trans isomers dodeca-2E, 4E, 8Z, 10E/Z-tetraenoic-acid-isobutylamide. At least 25 different alkylamides have been identified, and some have shown affinities to CB2 receptors. In *echinacea* species, cannabinoids are found throughout the plant structure but are most concentrated in the roots and flowers. Yangonin found in the kava plant is a ligand to the CB1 receptor. Tea (*camellia sinensis*) catechins also have an affinity for human cannabinoid receptors. A widespread dietary cannabinoid, beta-caryophyllene, a component from the essential oil of *cannabis* and other medicinal plants, has also been identified as a selective agonist of peripheral CB2 receptors in vivo. Black truffles also contain anandamide.

Most phyto-cannabinoids are nearly insoluble in water, but are soluble in lipids, alcohols, and other non-polar organic solvents.

Cannabinoids can be administered by many methods typically including but not limited to smoking, vaporizing, ingestion, transdermal sorption, sublingual sorption, or other mucosa sorption. Once in the body, most cannabinoids are metabolized in the liver, especially by cytochrome P450 mixed-function oxidases, mainly CYP 2C9. Thus, supplementing the inventive formulation with CYP 2C9 inhibitors may lead to extended or enhanced intoxication, incapacitation, or immobilization.

Cannabinoids can be separated from *cannabis* or other plants by extraction with organic solvents. Hydrocarbons and alcohols are often used as solvents. However, these solvents are extremely flammable and many are toxic. Butane may also be used, which evaporates extremely quickly. Supercritical solvent extraction with carbon dioxide is an alternative technique. Although this process requires high pressures, there is minimal risk of fire or toxicity, solvent removal is simple and efficient, and extract quality can be well controlled. Once extracted, cannabinoid blends can be separated into individual components using wiped film vacuum distillation or other distillation techniques. However, to produce high-purity cannabinoids, chemical synthesis or semi-synthesis is generally required.

Endo-cannabinoids are substances produced from within the body that activate cannabinoid receptors. After discovery of the first cannabinoid receptor in 1988, scientists began searching for an endogenous ligand for the receptor.

Endo-cannabinoids serve as intercellular "lipid messengers", signaling molecules that are released from one cell and activating the cannabinoid receptors present on other nearby cells. Although in this intercellular signaling role they are similar to the well-known monoamine neurotransmitters, such as acetylcholine and dopamine, endo-cannabinoids differ in numerous ways. For example, endo-cannabinoids are used in retrograde signaling between neurons. Furthermore, endo-cannabinoids are lipophilic molecules that are not readily soluble in water. They are not stored in vesicles, and exist as integral constituents of the membrane bilayers that make up cells. Endo-cannabinoids are believed to be synthesized "on-demand" rather than made and stored for later use. The mechanisms and enzymes underlying the biosynthesis of endo-cannabinoids remain elusive and continue to be an area of active research.

Conventional neurotransmitters are released from a "presynaptic" cell and activate appropriate receptors on a "postsynaptic" cell, where presynaptic and postsynaptic designate the sending and receiving sides of a synapse, respectively. Endo-cannabinoids, on the other hand, are described as retrograde transmitters because they most commonly travel "backward" against the usual synaptic transmitter flow. They are, in effect, released from the postsynaptic cell and act on the presynaptic cell, where the target receptors are densely concentrated on axonal terminals in the zones from which conventional neurotransmitters are released. Activation of cannabinoid receptors temporarily reduces the amount of conventional neurotransmitter released. This endo-cannabinoid mediated system permits the postsynaptic cell to control its own incoming synaptic traffic. The ultimate effect on the endo-cannabinoid-releasing cell depends on the nature of the conventional transmitter being controlled. For instance, when the release of the inhibitory transmitter GABA is reduced, the net effect is an increase in the excitability of the endo-cannabinoid-releasing cell. On the converse, when release of the excitatory neurotransmitter glutamate is reduced, the net effect is a decrease in the excitability of the endo-cannabinoid releasing cell.

Endo-cannabinoids are hydrophobic molecules, they cannot travel unaided for long distances in the aqueous medium surrounding the cells from which they are released, and therefore act locally on nearby target cells. Hence, although emanating diffusely from their source cells, they have much more restricted spheres of influence than do hormones which can affect cells throughout the body.

In 1992 the first such endo-cannabinoid compound was identified as arachidonoylethanolamine, and named anandamide ("AEA"). AEA is derived from arachidonic acid and has a pharmacology similar to THC, although its chemical structure is different. AEA has an affinity for CB1 receptors and to a lesser extent CB2, where it acts as a partial agonist. AEA is about as potent as THC at the CB1 receptor, and is found in nearly all tissues in a wide range of animals. AEA has also been found in plants, including small amounts in cocoa beans from which chocolate is made. Two analogs of AEA, 7, 10, 13, and 16-docosatetraenoylethanolamide and homo-γ-linolenoylethanolamine, have similar pharmacology. All of these are members of a family of signaling lipids called N-acylethanolamines, which also includes the non-cannabimimetic palmitoylethanolamide and oleoylethanolamide, which possess anti-inflammatory and orexigenic effects, respectively. Many N-acylethanolamines have also been identified in certain other plant seeds and also in mollusks.

Another endo-cannabinoid, 2-arachidonoylglycerol ("2-AG"), binds to both the CB1 and CB2 receptors with similar affinity, acting as a full agonist at both. 2-AG is present at significantly higher concentrations in the brain than AEA, causing some controversy whether 2-AG rather than AEA is chiefly responsible for endo-cannabinoid signaling in vivo. In particular, one in vitro study suggests that 2-AG is capable of stimulating higher G-protein activation than AEA, although the physiological implications of this finding are not yet known.

Discovered in 2000, N-arachidonoyl dopamine ("NADA") preferentially binds to the CB1 receptor. Like AEA, NADA is also an agonist for the vanilloid receptor subtype 1 (TRPV1), a member of the vanilloid receptor family. Outside the food industry, vanilloids which act at TRPV1 are used in so-called "pepper-spray" and/or other mace formulations.

In 2001, a fourth, ether type endo-cannabinoid, 2-arachidonyl glyceryl ether ("noladin ether") was isolated from porcine brain. Prior to this discovery, noladin ether had been synthesized as a stable analog of 2-AG; indeed, some controversy remains over 2-AGs classification as an endo-cannabinoid, as another group failed to detect the substance at "any appreciable amount" in the brains of several different mammalian species. Noladin ether binds to the CB1 receptor and causes sedation, hypothermia, intestinal immobility, mild reduced sensitivity to pain in mice, and binds weakly to the CB2.

A fifth endo-cannabinoid, virodhamine, or O-arachidonoyl-ethanolamine ("OAE"), was discovered in 2002. Although it is a full agonist at CB2 and a partial agonist at CB1, it behaves as a CB1 antagonist in vivo. In rats, OAE was found to be present at comparable or slightly lower concentrations than AEA in the brain, but peripherally in two-to-nine fold higher concentrations.

Recent evidence has highlighted lysophosphatidylinositol ("LPI") as the endogenous ligand to novel endo-cannabinoid receptor GPR55, making it a strong contender as the sixth endo-cannabinoid.

Historically, laboratory synthesis of cannabinoids were often based on the structure of herbal or phyto-cannabinoids, and a large number of analogs have been produced and tested. Synthetic-cannabinoids are particularly useful in experiments to determine the relationship between the structure and activity of cannabinoid compounds, by making systematic and incremental modifications of cannabinoid molecules. When synthetic-cannabinoids are used recreationally, they present significant health dangers to users. In the period of 2012 through 2014, over 10,000 contacts to poison control centers in the United States were related to use or abuse of synthetic-cannabinoids.

Medications containing natural or synthetic-cannabinoids or cannabinoid analogs include: Dronabinol (Marinol), which is Δ9-THC used as an appetite stimulant, anti-emetic, and analgesic; Nabilone (Cesamet, Canemes), a synthetic cannabinoid and an analog of Marinol; Rimonabant (SR141716), a selective CB1 receptor inverse agonist once used as an anti-obesity drug under the proprietary name Acomplia, and was also used for smoking cessation; CP-55940, produced in 1974 as a synthetic cannabinoid receptor agonist many times more potent than the phyto-cannabinoid THC; Dimethylheptylpyran (DMHP), an analog of phyto-cannabinoid THC; HU-210, about 100 times as potent as phyto-cannabinoid THC; HU-331, a potential anti-cancer drug derived from CBD that specifically inhibits topoisomerase II; SR144528, a CB2 receptor antagonist; WIN 55,212-2, a potent cannabinoid receptor agonist; JWH-133, a potent selective CB2 receptor agonist; Levonantradol (Nantrodolum), an anti-emetic and analgesic, but not currently in use in medicine; and AM-2201, a potent cannabinoid receptor agonist.

What is desired therefore is a method of humanely incapacitating or immobilizing a human or animal by providing a formulation including a cannabinoid which renders a recipient incapacitated or immobilized within a short period of time after dosing.

What is further desired is a delivery system which doses the recipient with the inventive formulation resulting in a tetrahydrocannabinol blood level of above at least approximately 1-250 milligrams per milliliter of whole blood for incapacitation, or at least approximately 250-500 milligrams per milliliter of whole blood for immobilization, and below a dosage which causes irreparable harm to or the death of the recipient.

What is additionally desired is a method of providing a delivery system to induce an incapacitating or immobilizing dose of the inventive formulation at a distance.

Further desired is a method of providing cannabinoid formulation wherein the formulation includes at least one antipsychotic or neroleptic such as but not limited to butyrophenones, phenothiazines, thioxanthenes, co-called atypical antipsychotics, and so-called second-generation antipsychotics to prevent or mitigate the violent psychosis of a formulation recipient.

What is also desired is a method of providing an inventive formulation which induces a lethal cannabinoid blood level in a recipient which causes the death of the recipient within a humane period of time after formulation administration.

SUMMARY OF THE INVENTION

It is therefore an object of the present invention to provide a method of humanely incapacitating a human or animal comprising providing a formulation including a cannabinoid which renders a recipient incapacitated within a short period of time after dosing, and providing a delivery system which doses the recipient with the formulation resulting in a tetrahydrocannabinol blood level of above at least approximately one-to-fifty milligrams per milliliter of whole blood (1-50 mg/ml) and below a dosage which causes irreparable harm to or death of the recipient.

Another objective of the present invention is to provide a method of humanely incapacitating a human or animal comprising, providing a formulation including a cannabinoid which renders within a short period of time a recipient incapacitated after administration of the formulation to the recipient, providing a delivery system which doses the recipient with the formulation inducing a tetrahydrocannabinol blood level of above at least approximately one-to-fifty milligrams per milliliter of whole blood (1-50 mg/ml) and below a dosage which causes irreparable harm to or death of the recipient, and wherein the formulation continues to render the recipient incapacitated for a long period of time without irreparable harm to or death of the recipient.

It is further an object of the present invention to provide a method of humanely immobilizing a human or animal comprising, providing a formulation including a cannabinoid which renders a recipient immobilized within a short period of time after dosing, providing a delivery system which doses the recipient with the formulation inducing a tetrahydrocannabinol blood level of above at least approximately two-hundred-and fifty and five-hundred and milligrams per milliliter of whole blood (250-500 mg/ml) and below a dosage which causes irreparable harm to or death of the recipient, and wherein the formulation continues to render the recipient immobile for a long period of time after dosing without irreparable harm to or death of the recipient.

It is yet another objective of the present invention to provide a method of humanely incapacitating or immobilizing a human or animal comprising, providing a formulation including a cannabinoid and a delivery system capable of dosing the recipient with the inventive formulation at a distance which renders a recipient incapacitated or immobilized within a short period of time after dosing, and wherein the recipient remains incapacitated or immobilized for a long period of time without causing irreparable harm to or the death of the recipient.

It is yet another objective of the present invention to provide a method of humanely incapacitating or immobilizing a human or animal comprising, providing a formulation including a cannabinoid and a delivery system capable of dosing the recipient with the inventive formulation at a distance which renders a recipient incapacitated or immobilized within a short period of time after dosing, and wherein the recipient remains incapacitated or immobilized for a long period of time without causing irreparable harm to or the death of the recipient.

Yet further, it is an objective of the present invention to provide a method of humanely incapacitating a human or animal comprising, providing a formulation including a cannabinoid which renders a recipient incapacitated within a short period of time after dosing, providing a delivery system which doses the recipient with the formulation resulting in a tetrahydrocannabinol blood level of above at least approximately one-to-fifty milligrams per milliliter of whole blood (1-50 mg/ml) and below a dosage which causes irreparable harm to or the death of the recipient, wherein the formulation includes at least one antipsychotic from the group consisting of antipsychotic or neuroleptic formulations including but not limited to butyrophenones, phenothiazines, thioxanthenes, atypical antipsychotics, second-generation antipsychotics, and combinations thereof.

Still further, an object of the present invention is to provide a method of humanely causing the death of a recipient comprising, providing a formulation wherein the formulation induces a lethal cannabinoid blood level in the recipient which causes the death of the recipient within a humane period of time after formulation introduction to the recipient.

DETAILED DESCRIPTION OF THE INVENTION

The inventive method provides a formulation delivery system configured for dosing a subject at a distance. The delivery system may include a dart-pistol or dart-rifle including a hypodermic dart including the inventive cannabinoid or cannabinoid based formulation. Both the dart-pistol and hypodermic dart may be any known so-called "dart-gun" system which is capable of dosing a recipient with the inventive formulation at a distance. It is contemplated that the inventive formulation may be primarily a cannabinoid based formulation. However, cannabinoids may be added to known sedative formulations to improve their safety and/or performance. Many and varied cannabinoid formulations may be innovated.

In an exemplary embodiment of the inventive formulation, an incapacitating dosage of tetrahydrocannabinol may be added to known effective dosages of propofol (diprivan). For healthy adults 55 years or younger, a general intravenous anesthetic infusion of diprivan is 40 mg every 10 seconds until induction onset. For general anesthetic use, a typical dose of diprivan is 2.0-2.5 mg per kilogram of recipient body weight, with a maximum dosage of 250 mg. However, delivery of diprivan at a distance makes it extremely difficult to guarantee an intravenous injection. Therefore, an intermuscular injection of approximately 150-250 mg of diprivan may be required to ensure almost instantaneous recipient incapacitation. By adding an appropriate dose of tetrahydrocannabinol to result in approximately one-to-fifty milligrams per milliliter of whole blood (1-50 mg/ml) of tetrahydrocannabinol, to the diprivan; once dosed, the recipient will be almost instantaneously incapacitated by the diprivan, within seconds, while the tetrahydrocannabinol dose will still further sedate the recipient for approximately another four-to-six hours, without depression of the body's autonomic functions.

If it is unnecessary to "immediately", or to "near-immediately", incapacitate a recipient, the inventive formulation may strictly consist of cannabinoids such as tetrahydrocannabinol. During instant inventor experimentation, an intermuscular injection of 5.0 mg of tetrahydrocannabinol rendered an overall healthy 50 year old, 100 kg male, fully incapacitated within 10-30 seconds, with its effects lasting approximately four-to-six hours.

The lethality of intravenous dosing of tetrahydrocannabinol in humans is typically unknown. As detailed in Marihuana, A Signal of Misunderstanding, a report delivered to the United States Congress by Raymond P. Shafer on Mar. 22, 1972 (herein incorporated by reference in its entirety), in laboratory animals, a dosage that caused death in 50% of subjects ("LD50") was in units of mg of tetrahydrocannabinol per kg of body weight. In mice and rats, an LD50 tetrahydrocannabinol dose is 28.6 mg per 42.47 kg of body weight. A dosage of approximately 1000 mg of tetrahydrocannabinol per kg of body weight is known to be the lowest intravenous dosage which causes death in laboratory animals. The typical lethal oral dosage of tetrahydrocannabinol is between approximately 225-450 mg per kg of body weight in laboratory animals.

Using intravenous administration, the acute one dose LD50 for tetrahydrocannabinol was 100 mg/kg in dogs and 15.6-62.5 mg/kg in monkeys depending on concentration of the solution. The minimal lethal intravenous dose for dogs, also depending upon concentration, was 25-99 mg/kg, and for monkeys 3.9-15.5 mg/kg.

In contrast to the delayed death observed in rats after oral administration, lethality in rats, dogs, and monkeys after intravenous injection occurred within minutes. When sublethal amounts were injected, central nervous system depression with concomitant behavioral changes similar to those observed after oral doses were observed. However, their onset was more rapid and the intensity of affect more severe with anesthesia, with convulsions noted after injection. Monkeys and dogs that survived the intravenous injection recovered completely within five to nine days.

The only consistent pathological changes noted were in animals which succumb. Pulmonary changes including hemorrhage, edema, emphysema, and generalized congestion were found—and death resulted from respiratory arrest and subsequent cardiac failure. The investigators presumed one mechanism possibly accounting for these findings was due to the concentration of the tetrahydrocannabinol solution and its insolubility in water. Presumably when these highly concentrated solutions mixed with blood, the tetrahydrocannabinol precipitated out of solution. The precipitated foreign material then formed aggregates (or emboli) that were filtered out in the lung capillaries causing a physical blockage of pulmonary blood flow.

Subsequently, intravenous studies were repeated using tetrahydrocannabinol emulsified in a sesame oil, polysorbate 80, or saline vehicles at 15 mg/ml or 40 mg/ml. The emulsions were administered at a uniform rate of 2 ml/15 sec. Doses administered were 1, 4, 16, 64, 92, 128, 192 and 256 mg/kg. All monkeys injected with 92 mg/kg or less survived and completely recovered from all effects within two to four days. An analogous intravenous dosage for a 100 kg human would be 9,200 mg (9.2 g) of near-pure tetrahydrocannabinol. All monkeys injected with 128 mg/kg or more succumb within thirty minutes for all but one subject, which took one-hundred-and-eighty minutes to expire. An analogous lethal intravenous dosage for a 100 kg human would be 12,800 mg (12.8 g) of near-pure tetrahydrocannabinol.

Histopathological changes found in the lungs of the deceased monkeys were like those described after the previous intravenous experiment. All monkeys that died exhibited severe respiratory depression and bradycardia within five minutes after injection. Respiratory arrest and subsequent cardiac failure occurred within minutes. Behavioral changes preceding death were salivation, prostration, coma, and tremors.

Behavioral and physiological changes described clinically in the surviving monkeys followed a consistent developmental sequence and were roughly dose related in severity and duration. Onset was fifteen minutes following injection and duration was up to forty-eight hours. Huddled posture and lethargy were the most persistent changes. Constipation, anorexia, and weight loss were noted. Hypothermia, bradycardia, and decreased respiratory rate generally were maximal two-to-six hours post injection. Tremors with motion but not at rest were believed to be caused by peripheral muscle inadequacy.

In summary, enormous intravenous doses of tetrahydrocannabinol, and all tetrahydrocannabinol and concentrated *cannabis* extracts ingested orally were unable to produce death or organ pathology in large mammals, but did produce fatalities in smaller rodents due to profound central nervous system depression.

The nonlethal oral consumption of 3 g/kg of tetrahydrocannabinol by a dog and monkey would be comparable to a 154-pound human eating approximately forty-six pounds, 21 kg, of one-percent THC *cannabis*, or ten-pounds of five-percent hashish, at one time. In addition, 92 mg/kg tetrahydrocannabinol intravenously produced no fatalities in monkeys. These doses would be comparable to a 154-pound human smoking at one time almost three pounds (1.28 kg) of one-percent THC *cannabis,* 250,000 times the usual smoked dose, and over a million times the minimal effective dose assuming fifty-percent destruction of the tetrahydrocannabinol by combustion.

Thus, evidence from animal studies and human case reports appears to indicate that the ratio of lethal-dose to effective-dose of tetrahydrocannabinol is quite large; and much more favorable than that of many other common psychoactive agents including alcohol, barbiturates, and opiates. This effective-to-lethal tetrahydrocannabinol dosage range may be exploited for medical, scientific, and industrial purposes.

Relatedly, known antipsychotic compounds may be included in the inventive cannabinoid formulation to prevent or mitigate quick onset and/or violent psychotic reactions to the inventive cannabinoids, especially tetrahydrocannabinol. Such known antipsychotic or neroleptic formulations include but are not limited to butyrophenones, phenothiazines, thioxanthenes, so-called atypical antipsychotics, and so-called second-generation antipsychotics.

The inventive method provides another apparatus or delivery system adapted for dosing a recipient with the inventive formulation at a distance. The delivery system may be a common paint-ball pistol or rifle. Utilizing the inventive formulation with the associated paint-balls (ammunition), a vaporizing or misting inventive formulation may be used. As the "paint-balls" burst on the front torso of a recipient, the resulting "cannabinoid cloud" soon to envelop the recipient's face and head will render the recipient incapacitated. The same apparatus or delivery system may also be used for animals.

Many and varied apparatus or inventive formulation delivery system types and techniques may be provided, such as but not limited to, non-lethal or less-than-lethal weapons such as hypodermic syringes, hypodermic darts, blowpipes, dart-pistols, dart-rifles, jab-sticks, dart-arrows, slingshots, mace, mace guns, paint-ball guns, flash-bag grenades, stun-shock grenades, gas canisters, deployable gas canisters, and combinations thereof.

Additionally, many and varied lethal weapons using modified ammunition and the inventive formulation may be used, such as but not limited to, single-shot, semi-automatic, or fully-automatic revolvers, pistols, shotguns, scatterguns, rifles, grenade launchers, rocket launchers, mortars, light artillery, heavy artillery, missile launchers, and combinations thereof.

Another exemplary embodiment of the inventive cannabinoid formulation and delivery system may be an improvement to known 'GPS wrist or ankle bracelets" used in Law Enforcement or Corrections for the remote tracking of a suspect, perpetrator, or inmate. The GPS bracelet would be affixed to the potential recipient of the cannabinoid formulation. Many varied inventive formulation administration scenarios are contemplated. If the bracelet wearer is incarcerated, the sedative cannabinoid formulation may be administered to the inmate during emergency situations, altercations, prison riots, escapes, and the like. Likewise, for probation and parole supervision, if an inventive cannabinoid formulation bracelet wearer travels outside a designated perimeter, or within the perimeter of a prohibited area (schools, drinking-establishments, restraining order perimeters, and the like), the bracelet type delivery system may incrementally administer the inventive cannabinoid formulation to "gracefully" bring the wearer to an incapacitated state, to prevent immediate incapacitation in case the wearer is driving a motor vehicle or other such action requiring cognizance. When the bracelet is "dosing activated", the bracelet may notify the authorities via wireless or cell-phone type transmission, so the wearer may be "apprehended".

In yet another exemplary embodiment of the inventive cannabinoid formulation and delivery system, a similar cannabinoid dosing bracelet may be placed on those being detained for investigation. If after affixing the inventive bracelet to a detainee, the detainee becomes aggressive, violent, or "bolts and runs", the detaining Officer may simply remotely activate the inventive bracelet which administers the inventive cannabinoid formulation to the detainee. In this scenario, the detaining Officer need not pursue the detainee. Rather, the recipient of the inventive cannabinoid formulation may be incapacitated in short order. Many and varied cannabinoid formulations and delivery systems for automatically dosing a recipient when certain criteria are met, may be realized.

Moreover, for long-term corrections and incarceration (such as life-in-prison terms of punishment), the inventive cannabinoid delivery system may be implantable within the body of a recipient. In this way, removing or disabling the delivery system would be nearly impossible by the "owner".

Additionally, water-borne, air-borne, and space-borne systems may also be used to effectively deliver the inventive formulation to a recipient.

While not wishing to be bound by any one theory or combination of theories, it is believed that, the combination, ratio, delivery system, method, or technique, dosage, dosage timing, dosage sequence, and in combination with other known sedatives; cannabinoids, and specifically THC, CBD, and CBN, may be exploited for industrial, scientific, and medical use.

Accordingly, this invention is not to be limited by the embodiments as described, since these are given by way of example only and not by way of limitation.

Having thus described several embodiments for practicing the inventive method, its advantages and objectives can be easily understood. Variations from the description above may and can be made by one skilled in the art without departing from the scope of the invention, which is to be determined from and by the following claims.

What is claimed is:

1. A method of humanely incapacitating a human or animal, the method comprising the steps of:
   providing a formulation including a cannabinoid;
   providing a delivery system comprising an injection step for dosing the recipient with the cannabinoid formulation resulting in a tetrahydrocannabinol blood level in the recipient of greater than one-to-fifty milligrams per milliliter of whole blood (1-50 mg/ml) and below a dosage which causes irreparable harm to or the death of the recipient; and
   immobilizing the recipient by using the delivery system to dose the recipient with said formulation.

2. The method of claim 1 wherein the formulation includes at least one dissociative anesthetic from the group consisting of benzodiazepines, barbiturates, opiates, diprivan, and combinations thereof.

3. The method of claim 1 wherein the formulation includes at least one anesthetic gas from the group consisting of benzodiapines, diprivan, thiopental, ketamine, desflurane, isoflurane, nitrous oxide, sevoflurane, xenon, and combinations thereof.

4. The method of claim 1 wherein the formulation includes at least one antipsychotic from the group consisting of antipsychotic or neroleptic formulations including butyrophenones, phenothiazines, thioxanthenes, atypical antipsychotics, second-generation antipsychotics, and combinations thereof.

5. The method of claim 1 wherein the delivery system comprises a hypodermic injection.

6. The method of claim 1 wherein the delivery system comprises a fluid, liquid, semi-solid, or solid.

7. The method of claim 1 wherein the delivery system doses the recipient with the formulation at a distance.

8. A method of humanely incapacitating or immobilizing a human or animal comprising:
   providing a formulation including a cannabinoid;
   providing a delivery system comprising an injection step capable of dosing the recipient with the formulation at a distance which renders a recipient incapacitated or immobilized within a short period of time after dosing, and wherein the recipient remains incapacitated or immobilized for a long period of time-after dosing without irreparable harm to or the death of the recipient; and
   immobilizing the recipient by using the delivery system to dose the recipient with said formulation.

9. The method of claim 1 wherein the delivery system provides the incapacitating dose of the formulation to the recipient without the recipient's knowledge until the onset of incapacitation of the recipient caused by the formulation.

10. A method of humanely incapacitating a human or animal comprising:
   providing a formulation including a cannabinoid which renders a recipient incapacitated after administration of the formulation to the recipient;
   providing a delivery system comprising an injection step which doses the recipient with the formulation inducing a tetrahydrocannabinol blood level of above at least approximately one to two-hundred-and-fifty milligrams per milliliter of whole blood (1-250 mg/ml) and below a dosage which causes irreparable harm to or the death of the recipient; and
   wherein the formulation continues to render the recipient incapacitated without irreparable harm to or the death of the recipient.

11. The method of claim 1, wherein the formulation includes a cannabinoid emulsified in sesame oil, polysorbate 80 or a saline vehicle.

12. The method of claim 11, wherein the concentration of the cannabinoid in the formulation ranges from 15 mg/ml to 40 mg/ml.

13. The method of claim 1, wherein the amount of the cannabinoid provided to the human or animal ranges from 1.0 mg to 25 mg.

14. The method of claim 1, wherein the amount of the cannabinoid provided to the human or animal ranges from 5.0 mg to 100 mg.

* * * * *